(12) United States Patent
Lund (10) Patent No.: US 8,852,171 B2
(45) Date of Patent: Oct. 7, 2014

(54) COMPACT BAG

(75) Inventor: Jesper G. Lund, Bagsvaerd (DK)

(73) Assignee: Coloplast A/S, Humlebaek (DK)

( * ) Notice: Subject to any disclaimer, the term of this patent is extended or adjusted under 35 U.S.C. 154(b) by 977 days.

(21) Appl. No.: 11/632,646

(22) PCT Filed: Jul. 14, 2005

(86) PCT No.: PCT/DK2005/000492
§ 371 (c)(1),
(2), (4) Date: Sep. 20, 2007

(87) PCT Pub. No.: WO2006/005349
PCT Pub. Date: Jan. 19, 2006

(65) Prior Publication Data
US 2008/0119803 A1    May 22, 2008

(30) Foreign Application Priority Data

Jul. 14, 2004 (DK) ................................. 2004 01107
Sep. 29, 2004 (DK) ................................. 2004 01486

(51) Int. Cl.
*A61F 5/44* (2006.01)
*A61M 27/00* (2006.01)

(52) U.S. Cl.
CPC ............ *A61F 5/4404* (2013.01); *A61M 27/008* (2013.01)
USPC .......................................... 604/544; 604/327

(58) Field of Classification Search
CPC .................................................. A61F 5/4404
USPC ............. 206/364, 69; 604/197, 327, 349, 544
See application file for complete search history.

(56) References Cited

U.S. PATENT DOCUMENTS

| 1,294,219 | A | * | 2/1919 | Andrus | ......................... 604/262 |
| 2,087,780 | A | * | 7/1937 | Powell | ............................ 604/262 |
| 2,289,032 | A | * | 7/1942 | Moffitt | ............................ 206/364 |
| 2,856,932 | A | * | 10/1958 | Griffitts | ........................ 604/171 |

(Continued)

FOREIGN PATENT DOCUMENTS

| DE | 2227416 | 12/1972 |
| DE | 19921555 | 2/2000 |

(Continued)

OTHER PUBLICATIONS

Office action dated Jan. 2, 2014 from European Patent Application No. 05758008.6 attached.

(Continued)

*Primary Examiner* — Melanie Hand
*Assistant Examiner* — Paula L Craig
(74) *Attorney, Agent, or Firm* — Coloplast Corp., Coloplast A/S; Nick Baumann (57) ABSTRACT

The present invention relates to a collecting device comprising a collecting device for collection of body fluids. The invention relates to a collecting device arranged in a compact configuration wherein the dimensions of the collecting device is small in comparison with the dimensions of the collecting device in an unfolded configuration. In particular the invention relates to a bag having an inner folding and an outer folding. Two pull points may further be arranged so that the application of oppositely directed forces to the first and second pull-points will lead to unfolding of the inner folding. With this arrangement the outer folding may be forced to unfold as the inner folding unfolds.

10 Claims, 7 Drawing Sheets

(56) References Cited

U.S. PATENT DOCUMENTS

| | | | | |
|---|---|---|---|---|
| 2,863,457 | A | * | 12/1958 | Barach .................... 604/350 |
| 3,030,958 | A | * | 4/1962 | Levin ...................... 604/347 |
| 3,131,812 | A | * | 5/1964 | Constant .................. 206/364 |
| 3,166,189 | A | * | 1/1965 | Disston .................... 206/364 |
| 3,200,415 | A | * | 8/1965 | Breece, Jr. ................ 4/144.2 |
| 3,312,221 | A | | 4/1967 | Overment |
| 3,329,261 | A | * | 7/1967 | Serany, Jr. et al. ......... 206/229 |
| 3,384,231 | A | * | 5/1968 | Cox et al. ................. 206/364 |
| 3,403,715 | A | * | 10/1968 | Trudel ..................... 604/317 |
| 3,478,743 | A | * | 11/1969 | Ericson .................... 604/33 |
| 3,495,706 | A | * | 2/1970 | Sokolic .................... 206/229 |
| 3,561,593 | A | * | 2/1971 | Ruda ....................... 206/554 |
| 3,608,268 | A | * | 9/1971 | Lauritzen .................. 53/452 |
| 3,648,704 | A | | 3/1972 | Jackson |
| 3,683,928 | A | * | 8/1972 | Kuntz ...................... 604/171 |
| 3,693,783 | A | * | 9/1972 | Hart ....................... 206/210 |
| 3,750,875 | A | * | 8/1973 | Juster ..................... 206/364 |
| 3,762,399 | A | | 10/1973 | Riedell |
| 3,781,922 | A | * | 1/1974 | Ericson .................... 4/144.1 |
| 3,892,311 | A | * | 7/1975 | Sneider .................... 206/229 |
| 4,031,897 | A | | 6/1977 | Graetz |
| 4,062,363 | A | * | 12/1977 | Bonner, Jr. ................ 604/171 |
| 4,116,338 | A | * | 9/1978 | Weichselbaum .............. 206/438 |
| 4,126,135 | A | | 11/1978 | Hinman, Jr. |
| 4,160,505 | A | * | 7/1979 | Rauschenberger ........... 206/571 |
| 4,204,527 | A | * | 5/1980 | Wu et al. .................. 600/575 |
| 4,226,328 | A | * | 10/1980 | Beddow .................... 206/364 |
| 4,230,115 | A | | 10/1980 | Walz, Jr. et al. |
| 4,379,506 | A | * | 4/1983 | Davidson ................... 206/364 |
| 4,685,913 | A | * | 8/1987 | Austin ..................... 604/349 |
| 4,811,847 | A | * | 3/1989 | Reif et al. ................ 206/571 |
| 4,955,879 | A | | 9/1990 | Mervine |
| 5,009,649 | A | * | 4/1991 | Goulter et al. ............. 604/351 |
| 5,065,459 | A | | 11/1991 | Tjahaja et al. |
| 5,147,341 | A | * | 9/1992 | Starke et al. .............. 604/349 |
| 5,176,152 | A | * | 1/1993 | Wheeler .................... 128/844 |
| 5,205,298 | A | * | 4/1993 | Hurst ...................... 128/844 |
| 5,242,398 | A | * | 9/1993 | Knoll et al. ............... 604/103.05 |
| 5,406,650 | A | * | 4/1995 | Einbinder .................. 4/144.2 |
| 5,511,557 | A | * | 4/1996 | Hazard et al. .............. 600/573 |
| 5,582,599 | A | * | 12/1996 | Daneshvar .................. 604/263 |
| 5,662,630 | A | * | 9/1997 | Raynie ..................... 604/349 |
| 5,711,445 | A | * | 1/1998 | Robbins, III ............... 220/8 |
| 5,745,926 | A | * | 5/1998 | Cailleteau ................. 4/144.1 |
| 5,988,386 | A | * | 11/1999 | Morrow ..................... 206/581 |
| 6,004,305 | A | | 12/1999 | Hursman et al. |
| 6,053,313 | A | * | 4/2000 | Farrell et al. ............. 206/364 |
| 6,116,780 | A | * | 9/2000 | Young et al. ............... 383/44 |
| 6,355,004 | B1 | * | 3/2002 | Pedersen et al. ............ 600/581 |
| 6,659,986 | B1 | * | 12/2003 | Nilstein ................... 604/317 |
| 6,840,379 | B2 | * | 1/2005 | Franks-Farah et al. ........ 206/571 |
| 6,858,021 | B2 | * | 2/2005 | Washington ................. 604/265 |
| 6,887,223 | B2 | * | 5/2005 | Bisbee ..................... 604/353 |
| 6,887,230 | B2 | * | 5/2005 | Kubalak et al. ............. 604/544 |
| 7,682,353 | B2 | * | 3/2010 | Tanghoj et al. ............. 604/544 |
| 8,328,792 | B2 | * | 12/2012 | Nishtala et al. ............ 604/544 |
| 2001/0049520 | A1 | * | 12/2001 | Robertson et al. ........... 604/544 |
| 2002/0193762 | A1 | * | 12/2002 | Suydam ..................... 604/327 |
| 2003/0004496 | A1 | * | 1/2003 | Tanghoj .................... 604/544 |
| 2003/0018322 | A1 | * | 1/2003 | Tanghoj et al. ............. 604/544 |
| 2003/0046753 | A1 | * | 3/2003 | Buttigieg .................. 4/144.1 |
| 2003/0055403 | A1 | | 3/2003 | Nestenborg et al. |
| 2003/0060807 | A1 | | 3/2003 | Tanghoj et al. |
| 2003/0150050 | A1 | | 8/2003 | Tanaka |
| 2004/0236293 | A1 | * | 11/2004 | Tanghoj et al. ............. 604/327 |
| 2005/0043715 | A1 | * | 2/2005 | Nestenborg et al. .......... 604/544 |
| 2009/0163884 | A1 | * | 6/2009 | Kull-Osterlin et al. ....... 604/328 |

FOREIGN PATENT DOCUMENTS

| | | |
|---|---|---|
| FR | 2731345 | 9/1996 |
| GB | 2296440 | 7/1996 |
| JP | 63-286156 | 11/1988 |
| JP | 2004359255 | 11/1988 |
| JP | 9-10284 | 1/1997 |
| JP | 2002-381670 | 3/2004 |
| JP | 2004359255 | 12/2004 |
| WO | WO02102288 | 12/2002 |
| WO | WO 03/002179 A2 | 1/2003 |
| WO | 2004054446 | 7/2004 |
| WO | WO 2004100842 | * 11/2004 |

OTHER PUBLICATIONS

Extended European search report in the corresponding EP application No. 10179266.1, dated Dec. 10, 2010.

English translation of JP Office action, dated Jul. 16, 2010.

* cited by examiner

COMPACT BAG

This is a national stage of PCT/DK05/000492 filed Jul. 14, 2005 and published in English.

FIELD OF THE INVENTION

The present invention relates to a collecting device comprising a collecting device for collection of body fluids. The invention relates to a collecting device arranged in a compact configuration wherein the dimensions of the collecting device is small in comparison with the dimensions of the collecting device in an unfolded configuration.

In particular the invention relates to a bag having an inner folding and an outer folding. Two pull points may further be arranged so that the application of oppositely directed forces to the first and second pull-points will lead to unfolding of the inner folding. With this arrangement the outer folding may be forced to unfold as the inner folding unfolds.

BACKGROUND OF THE INVENTION

For a large group of persons intermittent catheterisation is a daily-life procedure, taking place several times a day. Typically catheters for intermittent catheterisation are used by patients suffering from urinary incontinence or by disabled individuals like para- or tetraplegics who may have no control permitting voluntary urination and for whom catheterisation may be the way of urinating. Using an intermittent catheter, the bladder may be drained through a natural or artificial urinary canal.

The availability of catheter assemblies, which are compact and discrete to carry along and dispose via the garbage collection in addition to being easy to use, even for individuals with reduced dexterity, significantly improves quality of life for a large group of individuals. Among such compact catheters can Compact Female be mentioned, which is produced by Coloplast A/S.

WO 03/002179 discloses a urinary catheter device which is adapted for a configuration wherein the length of the catheter is reduced relative to the length of the catheter in a configuration suitable for insertion of the catheter in the urethra. Thus the catheter may be stored and carried along in a compact and discrete configuration.

In some situations a user may wish to use a catheter with a urine bag connected to it, e.g. when a patient in a wheel chair is unable to move from the wheelchair to the toilet. Urine bags are typically made from sheets of a foil material joined along the edges. The thickness of the urine bag is thus very small, but due to the plane dimensions of the urine bag, it is not a discrete unit to carry along.

DESCRIPTION OF THE INVENTION

It is an object of the present invention to provide a collecting device such as a urine bag device which is compact and discrete to carry along and is easy to use, even for individuals with reduced dexterity. The collecting device comprises a collecting bag, such as a urine bag. However, the invention is not limited to a collecting bag, such as a urine bag, but can be applied to any type of bag, which can be compacted.

In order to provide such a discrete, compact and easy to use collecting device a method for folding and unfolding a bag, such as the collecting bag, is provided. Such a method for folding a bag into a compact state, comprises steps for, compacting the collecting bag from a non-compact to a semi-compact state by packing the collecting bag in a first direction, compacting the collecting bag from the semi-compact state to the compact state by packing the collecting bag in a second direction different from the first direction, and that when the bag is unfolded a first force is applied to a first area of the collecting bag and a second force is applied to a second area of the bag, the first and second area are arranged on opposite sides of the collecting bag with reference to the first direction.

In one embodiment the step for compacting the bag from the non-compact state to the semi-compact state comprises folding the collecting bag in the first direction around at least one folding line. The folding line will then advantageously work as stiffening means during unfolding of the bag and thereby aid in the unfolding process and moreover help to keep the bag unfolded.

In yet another embodiment the step for compacting the bag from the non-compact state to a semi-compact state furthermore comprises folding the bag around at least two folding lines, and the bag is consecutively folded clockwise and counter-clockwise around the at least two folding lines.

By providing multiple folding lines that act as stiffening means the compacted bag is even more easily unfolded. By folding the bag shiftily clockwise and counter-clockwise around the folding lines the bag is likewise easy to unfold as it is possible to be able to get hold of two opposite areas on the bag which can be pulled apart.

Advantageously a method for unfolding a bag folded according to the method of any one of the claims is thereby provided wherein a first force is applied to a first area of the bag and a second force is applied to a second area of the bag and that the first and second area are separated by the at least one folding line, the first and second force having different directions. Thus easy unfolding of the bag is provided where only one pull direction is required.

In practice the first area can be held stationary by a hand while the second area is pulled away from the first area. Thereby the first force is applied to the first area in the form of a reaction to the second force, the action of pulling away, applied to the second area.

The bag can be folded in a number of different ways. For example in the step for compacting the bag from the non-compact state to a semi-compact state comprises crumpling the bag in the first direction.

Furthermore the step for compacting the bag from the semi-compact state to the compact state comprises rolling, folding or crumpling the bag in the second direction.

The invention thus discloses a bag adapted to be compacted in a first direction and second direction wherein a first area of the bag and a second area of the bag is placed opposite each other when seen in the first direction, the bag furthermore comprising a first pull point arranged at the first end of the bag and a second pull point arranged at the second end of the bag. This advantageously provides a bag that can be unfolded by separating the tabs in only one direction.

The bag can furthermore be connected to a constraining element for constraining the bag in its compacted state. Alternatively or additionally the bag can be connected to a connector for connecting a catheter.

A constraining element is furthermore provided by the invention. The constraining element is arranged to at least partly constrain a bag in a compact state wherein at least one area of the constraining element is attached to an area of the bag.

Preferably the constraining element comprises a compartment for at least partly accommodating the bag, such a constraining element can for example be a tubular element.

In one embodiment a connector for connecting a catheter is arranged on an area of the constraining element, typically communication is provided between the connector and the bag. This allows for media, typically a fluid such as urine to flow from a catheter into the bag.

Accordingly a urine bag device is provided, said urine bag device comprising a urine bag for collection of urine, wherein said urine bag is arranged in a compact configuration.

Advantageously the collecting bag is compacted into a compact state according to the methods as described above.

A urine bag device according to the invention may be provided in the shape of a one-piece package comprising only one urine bag in a compact configuration. In the compact configuration the urine bag is handy and discrete to carry along. The urine bag device may e.g. be of a cylinder-like shape and have a size so that a major part of the device may be covered by a hand or the urine bag device may fit into a trouser pocket. Thus the size and shape of the urine bag device may correspond to that of a mobile phone or other objects typically found in a handbag and the urine bag may then be provided in a device with a discrete and non-medical appearance. The urine bag device may also be provided in a pouch-like shape, e.g. in a size and appearance similar to a one-piece sanitary towel, such that the device may fit into a trouser pocket.

In order to evaluate the compactness of urine bag in the compact configuration, the enveloping surface of the urine bag in the compact configuration may be considered. The enveloping surface of a given object may be defined as an imaginary surface enveloping said object and having the smallest possible surface area. The dimensions of the object may then be defined as the dimensions of said enveloping surface of said object.

When the object is folded in the first direction and folded in the second direction the object can in its compact configuration be enveloped by a cube. In this configuration the length of a given object may be defined as the maximum dimension of said object. The thickness of the object may be defined as the minimum dimension of the object. The enveloping surface of the urine bag would thereby be considered to be all the six square surfaces of the cube.

When the object is folded in the first direction and rolled in the second direction the object can in its compact configuration be enveloped by a cylinder. The enveloping surface of the urine bag would thereby be considered to be the circumferential surface and the two circular end surfaces of the cylinder.

The urine bag may be arranged in a compact configuration, wherein the enveloping surface of the urine bag in the compact configuration has a surface area less than 20% of the surface area of the urine bag. Also the urine bag device may have a surface area less than 20% of the surface area of the urine bag. The enveloping surface of the urine bag in the compact configuration and/or said urine bag device may even have a surface area less than 15%, such as less than 10%, such as less than 8%, such as less than 6% or even less than 5%.

In theory it can be understood that a urine bag which first is folded three times in the first direction and afterwards folded three times in the second direction would have an enveloping surface which is only one ninth, approximately 11%, of the surface area of the urine bag in its non-compacted state if the thickness is considered to be negligible.

However, if we consider a urine bag having a height of 13.3 cm, a width of 19.8 cm and a thickness of 0.1 cm when in its non-compacted state we can obtain a considerably more accurate number. When the urine bag is in its non-compacted state it will have an enveloping surface of [2*(13.3 cm*19.8 cm)]+[2*(0.1 cm*13.3 cm)]+[2*(0.1 cm*19.8 cm)]=533.3 cm$^2$.

When folded three times in the first direction into its semi-compact state the bag will measure 13.3 cm in height, 6.6 cm in width and 0.3 cm in thickness. This will result in an enveloping surface of 187.5 cm$^2$.

Finally, when folded three times in the second direction, into the bags compact state, the bag will measure 4.4 cm in height, 6.6 cm in width and 0.9 cm in thickness. This will result in an enveloping surface of 77.88 cm$^2$. Accordingly it can be deduced that the enveloping surface of the urine bag in its compact state is (77.88 cm$^2$/533.3 cm$^2$)*100%=14.6% the size of the urine bag in its non-compact state.

Alternatively a urine bag having the same dimensions and which is folded three times in the first direction and then rolled into a compact configuration which can be enveloped by a cylinder measuring 6.6 cm in height and 0.5 cm in radius. This results in an enveloping surface of 2*pi*6.6 cm*0.5 cm=20.7 cm$^2$.

Since the enveloping surface of the urine bag in its non-compact state still is 559.78 cm$^2$ the enveloping surface of the urine bag in its compact state is (20.7 cm$^2$/559.78 cm$^2$)*100%=3.7% of the non-compact size.

However, if we consider a urine bag having a height of 13.3 cm, a width of 19.8 cm and a thickness of 0.5 cm when in its non-compacted state we can obtain a considerably more accurate number. When the urine bag is in its non-compacted state it will have an enveloping surface of [2*(13.3 cm*19.8 cm)]+[2*(0.5 cm*13.3 cm)]+[2*(0.5 cm*19.8 cm)]=559.78 cm$^2$.

The urine bag may comprise at least one wall defining a cavity for containing a liquid, the urine bag further comprising at least one inlet opening in communication with said cavity, such that liquid may enter the cavity through the inlet opening. The walls are typically provided in a flexible material, such as a polymer film i.e. PolyVinyleCloride, PolyEthylene, PolyPropylene, PolyAmide, ThermoPlastic Elastomers or any sandwich configuration comprising any of the mentioned materials.

The urine bag may e.g. be made from sheets of a foil material joined along the edges to define said cavity, possibly leaving a minor part of the edges un-joined to define said inlet opening.

The urine bag may be an essentially two-dimensional construction in the sense that the walls of the urine bag when unfolded lie roughly in a plane. The thickness of the urine bag is thus negligible compared to the dimensions of the urine bag in the plane, i.e. the main dimensions of the urine bag. An essentially two-dimensional urine bag may e.g. comprise two opposing walls of similar size joined along the edges. A urine bag may also be a three dimensional construction in the sense that the walls of the urine bag when unfolded defines a three dimensional object in the sense that no dimension is negligible in comparison with the others. In other words the urine bag cannot be flattened without folding the walls. A three-dimensional urine bag will typically be stored in a flattened configuration. The relevant dimensions and surface area for comparison with a compact configuration of the urine bag may in this case relate to the flattened urine bag. Thus the dimensions and the surface area of the 'unfolded' urine bag may be defined by the enveloping surface of the flattened urine bag.

In one embodiment of the invention the urine bag is folded from said unfolded or flattened configuration to obtain said compact configuration. The folding may include folding, pleating, rolling and/or crumpling up the urine bag.

In the compact configuration the main dimensions of the urine bag are typically reduced but the thickness may be increased as compared to the dimensions of the urine bag. However the absolute increase in thickness will typically be much smaller than the reduction of the other dimensions, so that the urine bag appears more compact in the compact configuration, i.e. the volume of the urine bag is mainly the same but the maximum extent of the urine bag has been reduced.

In one embodiment of the invention any dimension of the enveloping surface of the urine bag in the compact configuration and/or the enveloping surface of the urine bag device is substantially smaller than the length of the urine bag.

In one embodiment of the invention any dimension of the urine bag in the compact configuration is essentially half the length of the urine bag or less. This is e.g. obtainable by folding the bag into a compact configuration, said folding comprising a V-fold with a folding line dividing the length of the bag in two. The folding may further comprise additional folding, pleating, rolling or crumpling up of the bag to reduce other dimensions exceeding in length half the length of the urine bag.

In one embodiment of the invention any dimension of the urine bag in the compact configuration is essentially one third the length of the urine bag or less. This is e.g. obtainable by a folding of the bag into a compact configuration, said folding comprising a Z-fold with folding lines dividing the length of the bag in three. The folding may further comprise additional folding, pleating, rolling or to crumpling up of the bag to reduce other dimensions exceeding in length one third of the length of the urine bag.

For the user a very important parameter is the dimensions of the urine bag device comprising the urine bag in the compact configuration. The dimensions of the urine bag device may typically be similar to the dimensions of the urine bag in the compact configuration.

Alternatively the urine bag device can have half the length of the urine bag. The urine bag device may even be one third the length of the urine bag or less.

In one embodiment of the invention the urine bag is folded so as to support full unfolding by application of a force to a first pull point of the urine bag, typically while a second pull point of the urine bag is kept fixed by application of an oppositely directed force. The force is typically a pull, but may also be a push. As a result of the application of said force the first pull-point is displaced away from the second pull point. The second pull point may e.g. be situated at the opening of the urine bag. The first pull-point may be situated at an edge of the urine bag opposite to the first pull-point. Gripping means may be attached to the first pull point to facilitate application of the force and to clearly indicate where to apply the force. The second pull point may be attached to the constraining means.

The urine bag may suitably be folded so that in the compact configuration of the urine bag the pull points or at least the gripping means of the pull points are easily accessible from the outside of the urine bag device. In the compact configuration of the urine bag the first and the second pull point may e.g. be present at opposite ends of the urine bag device. When the pull points are situated at opposite ends of the urine bag, this may be obtained by a folding of the urine bag comprising a Z-fold, such that opposite ends of the urine bag are present at opposite ends of the urine bag device.

For some embodiments of the invention it is advantageous that both pull points are situated at the same end of the urine bag device. This may be obtained by a folding of the urine bag comprising a V-fold or a W-fold, so that opposite ends of the urine bag device are present at the same end of the urine bag device.

In one embodiment of the invention the folding of the urine bag comprises an inner folding and an outer folding. When folding the urine bag into the compact configuration, the inner folding is the first folding to be made, wherein the urine bag is folded from its non-compact state to its semi-compact state, and is followed by the outer folding, wherein the urine bag is folded from its semi-compact state to its compact state. The pull points may further be arranged so that the application of oppositely directed forces to the first and second pull-points will lead to unfolding of the inner folding. With this arrangement the outer folding may be forced to unfold as the inner folding unfolds.

In one embodiment of the invention the inner folding comprises a Z-fold. The folding may further comprise an outer folding comprising one or more V-folds, pleating or rolling of the Z-folded urine bag, said outer folding having fold-lines perpendicular to the fold lines of the Z-fold. As previously discussed the Z-fold may be advantageous for obtaining a urine bag device wherein the first and second pull points are present at opposite ends of the urine bag device. The inner folding may also comprise a V-fold or a W-fold, in which case a urine bag device may be obtained wherein the first and second pull points are present at the same end of the urine bag device.

Figure 11:
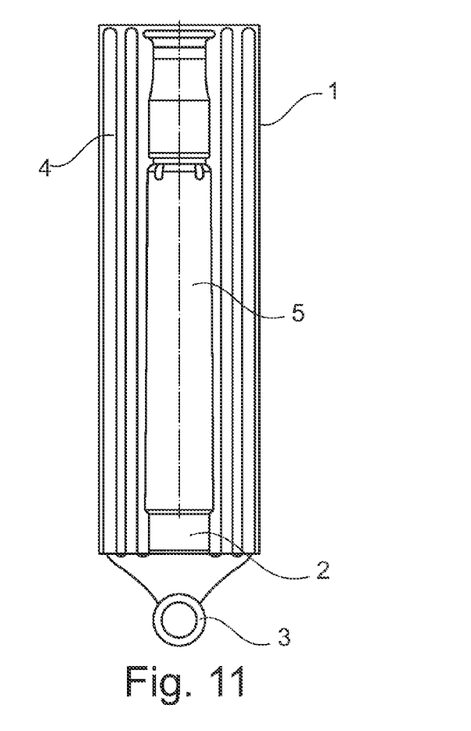
FIG. 11 illustrates a third embodiment of a catheter assembly according to the invention.

The urine bag may also be folded into itself, such that one part of the urine bag forms a pocket inside another part of the urine bag as can be seen in FIG. 11. The urine bag or a part of the urine bag may even be crumpled up like a sleeping bag. This may be done so that the opening of the urine bag is present at one end of the urine bag device and the first pull point is present at the opposite end of the urine bag device or at the same end of the urine bag device.

The urine bag device may comprise constraining means for constraining the urine bag in the compact configuration. The constraining means may suppress the tendency of a folded urine bag to unfold, hence fixating the urine bag in the compact configuration. The constraining means may be a string, a belt, a piece of tape or a sticker positioned so as to hold the urine bag together in the compact configuration. The constraining means may cover at least a major part of the urine bag in the compact configuration. In this case the constraining means may constitute a protective cover, protecting the urine bag from damage and dirt from the environment. The constraining means may even cover the entire urine bag. This has the advantage that the urine bag may be provided in a sterile condition. The urine bag device may however also comprise an outer package. In this case the urine bag may be provided in clean or sterile condition even if the constraining means cover only a portion of the urine bag.

In one embodiment of the invention the constraining means is a sleeve member adapted to encircle at least a part of the urine bag in the compact configuration. The urine bag device thus comprises a urine bag provided in the compact configuration inside the sleeve member. The arrangement may e.g. be so that the opening of the urine bag is situated at one end of the sleeve member. The sleeve member typically covers at least a major part of the urine bag in the compact configuration. The sleeve member may e.g. be long enough to surround the full length of the urine bag in the compact configuration.

The sleeve member may have two open ends or it may be closed in one or two ends, e.g. by a joint between opposite edges of the open end or by a removable closure. The sleeve member may further be closed so as to envelope the urine bag in the compact configuration.

The sleeve member may be made of a soft, thin material like a plastic bag. The sleeve member may also be provided in the shape of a relatively rigid tube. This provides good protection for the urine bag against damage, e.g. when the urine bag is kept in a handbag with other articles, some of which may have sharp edges.

In one embodiment of the invention the urine bag is releasable from the constraining means by application of a releasing force to a first release point of the urine bag. The releasing force may be a pull or a push. In order to prevent translational movement of the urine bag device a second release point of the urine bag and/or the constraining means may be kept fixed by application of a force oppositely directed to the force applied to the first release point. The urine bag is releasable from the constraining means in the sense that the bag is allowed to unfold from the compact configuration. Thus the contact between the constraining means and the urine bag may remain even after the urine bag is released. The constraining means may even form part of the urine bag in the sense that urine may be conducted through the constraining means. The constraining means may also be removable from the urine bag.

The urine bag may be folded so that the release point in the compact configuration of the urine bag is easily accessible from the outside of the urine bag device.

The urine bag may have a handgrip at the release point, such as a ring, a flap, a string etc. to facilitate the pull. This is advantageous for users of reduced dexterity and further clearly indicates where to pull.

As an example the urine bag device may comprise constraining means in the shape of a sleeve member and the urine bag may be pulled out of the sleeve member by pulling in a release point of the urine bag, while an oppositely directed force are applied to the constraining means.

Typically a urine bag will remain at least partly folded after the urine bag is released from the constraining means. The user then has to fully unfold the urine bag before use, which may be a disadvantage for users having reduced dexterity.

In one embodiment of the invention the urine bag is folded so as to support full unfolding by application of the releasing force to the release point, i.e. the forces applied to fully unfold the urine bag may also be the releasing forces, the first release point and the first pull point being identical. Thus the urine bag may be released from the constraining means and fully unfolded by the application of a force to said release or pull point of the urine bag, e.g. by pulling at said point.

In one embodiment of the invention the urine bag device comprises a connector for connecting the urine bag device to a urinary catheter device. The connector are suitably placed at the opening of the urine bag, so that urine may be conducted from the urinary catheter device and into the urine bag.

However, fluid communication between the urinary catheter device and the urine bag can also be provided in a number of other ways, for example by connecting the opening of the urine bag to one end of the sleeve, while the connector is mounted on the other end of the sleeve.

The urinary catheter device may comprise an external catheter, such as a urisheath or an internal catheter, e.g. an intermittent catheter or an indwelling catheter, the internal catheter being for urethral or suprapubic use. A urine bag device according to the invention may in particular be used with a compact intermittent catheter similar to the catheter device disclosed in WO 03/002179, which is hereby incorporated by reference.

The connector may be attached or attachable to the urinary bag or to the constraining means. The connector should ensure that urine may be conducted from the catheter to the urine bag without spillage. The connector may thus advantageously provide a liquid tight passage from the catheter to the urine bag, e.g. by providing a liquid tight seal between the connector and the urinary catheter and between the connector and the urine bag.

One aspect of the invention relates to a catheter assembly comprising a urine bag device with any feature previously described and a urinary catheter device. The urinary catheter device may e.g. comprise an intermittent catheter.

In one embodiment of the invention, the urine bag device is attachable to the urinary catheter device by means of the connector for connecting the urine bag device to the catheter device. This has the advantage that a user has the option of using the catheter device with or without the urine bag.

In another embodiment of the invention the urine bag device is attached to the urinary catheter device in fixed connection. An advantage of this embodiment is elimination of the risk that the user fails to connect the catheter device and the urine bag device properly.

In one embodiment of the invention the urine bag device and the urinary catheter device is adapted to be positioned side by side. This provides for storage of the assembly in a compact configuration. The connector for connecting the urine bag device and the urinary catheter device may be flexible so as to support bending. The connector may e.g. comprise a flexible hose, e.g. a corrugated hose. This is particularly advantageous when the catheter assembly is provided with the urine bag device attached to the urinary catheter device.

In another embodiment of the invention the catheter assembly is adapted for a configuration wherein the urine bag device is positioned in extension of the urinary catheter device.

In another embodiment of the invention the urine bag device is adapted to encircle the urinary catheter device. The catheter assembly may e.g. be provided with the urine bag device in a compact configuration encircling the urinary catheter device.

Another aspect of the invention relates to a method of folding a urine bag, said method comprising the steps of:
1. providing a urine bag with an opening in one end and a pull point in an opposite end,
2. folding the bag in an inner folding, said inner folding having fold lines dividing the urine bag in sectors such that the opening of the urine bag belongs to one sector and the pull point belongs to another sector,
3. folding the bag in an outer folding, the foldlines of said outer folding being perpendicular to the fold lines of said inner folding.

The inner folding may comprise a Z-fold. The outer folding may comprise rolling or pleating the bag or folding the bag in one or more V-folds.

When unfolded the sector wherein the opening of the urine bag is held in place and the pull point is pulled away from the opening. The urine bag is thereby unfolded in a simple action and is ready to be used.

The principle of the invention can be used in other applications i.e. disposable bags for consumer purposes such as doggy bags, picnic waste bags, house hold waste bags or the like. Another use of the invention could be in any field of products that consists of thin plastic film/foil or paper that in an unfolded configuration causes difficulties in storage or transportation i.e. sheaths for "bed wetters", sanitary towels, raincoats, or table protection sheaths.

DETAILED DESCRIPTION OF THE INVENTION

Preferred embodiments of the invention will now be described in details with reference to the drawing in which.

Figures 1, 2, 3:
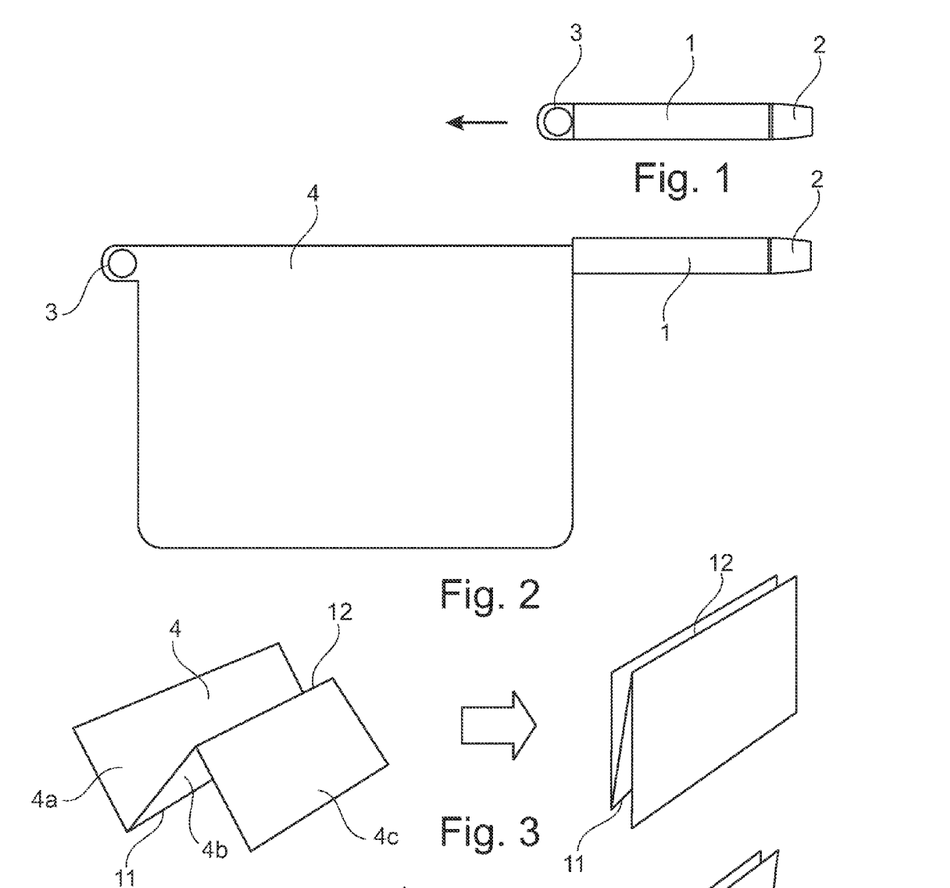
FIG. 1 illustrates a first embodiment of a urine bag device according to the invention, wherein the urine bag is in a compact configuration.
FIG. 2 illustrates the same embodiment of the invention, wherein the urine bag is unfolded for use.
FIG. 3 illustrates a Z-fold

FIG. 1 shows a urine bag device according to the invention, wherein the urine bag 4 is provided in a compact configuration inside the constraining means, such as sleeve member 1. A connector 2 extends from one end of the sleeve member 1. The connector may be attached to the constraining means and/or the urine bag. From the opposite end of the sleeve member 1 a handgrip 3 is sticking out at the first pull point of the urine bag 4, the urine bag being provided in a compact configuration inside the sleeve member 1. By pulling in the handgrip in the direction indicated by the arrow, the urine bag is released from the sleeve member 1.

FIG. 2 shows the urine bag device of FIG. 1 after the urine bag has been released from the sleeve member. The connector 2 and the urine bag 4 extend from opposite ends of the sleeve member 1. The dimensions of the urine bag device with the urine bag provided in a compact configuration as shown in FIG. 1 is substantially smaller than the length of the urine bag in use as illustrated in FIG. 2.

Figure 4:
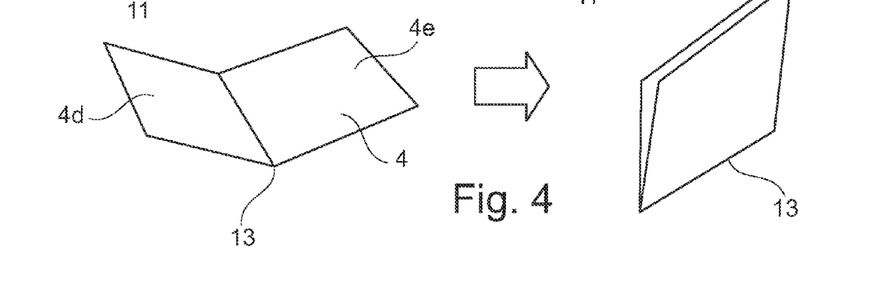
FIG. 4 illustrates a V-fold
Figure 5:
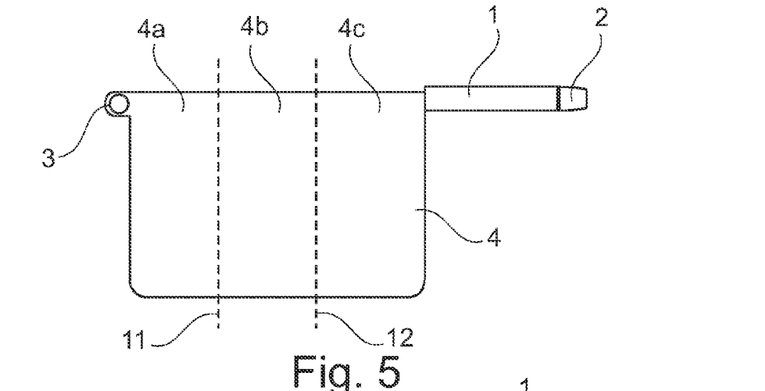
FIG. 5-8 illustrates a folding of the urine bag.
Figure 6:
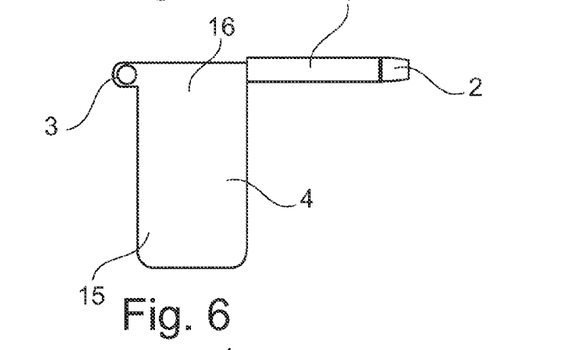
Figure 7:
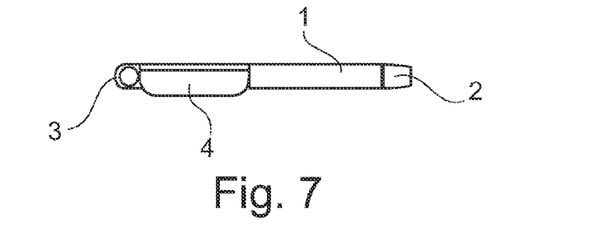
Figure 8:
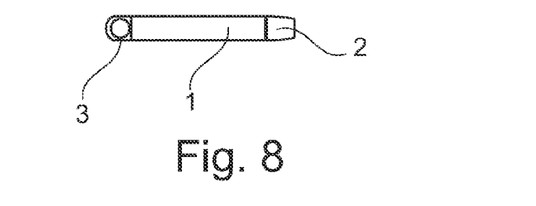

FIGS. 3 and 4 show different types of folding. FIG. 3 shows a Z-fold which has two fold lines 11 and 12 and FIG. 4 illustrates a V-fold having one fold line 13. The limbs 4a,4b, 4c,4d,4d of the folds may be unequal, however a folding with essentially equal limbs will typically be more size economic.

FIG. 5-8 illustrates a folding of the urine bag. The unfolded urine bag is first folded in a clockwise and counter-clockwise manner into a Z-fold with the fold lines indicated by dashed lines 11 and 12. Secondly the Z-folded urine bag is rolled from the lower end 15 of the Z-folded bag to the upper end 16. Finally the urine bag is pushed inside the sleeve member 1. The urine bag has a neck extending inside the sleeve member, the neck being attached to the connector 2. The neck is adapted to be crumpled or folded up inside the sleeve member allowing the urine bag to be pushed into the sleeve member to arrive at the compact arrangement shown in FIG. 8. This folding of the urine bag supports full unfolding of the urine bag by application of a pull to the pull point with the gripping means 3 while holding the sleeve member. The position of the pull point 3 ensures that the bag does not twist when pulling at the gripping means.

Figure 9:
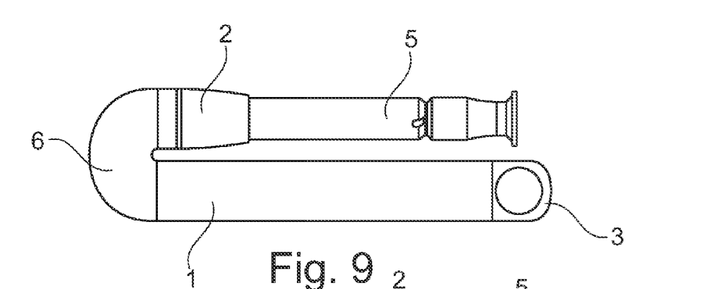
FIG. 9 illustrates a first embodiment of a catheter assembly according to the invention.

FIG. 9 shows a catheter assembly comprising a intermittent catheter device 5 similar to the device disclosed in WO 03/002179, FIGS. 15-18. The catheter device is attached to the sleeve member 1 of the urine bag device via the connector 2. The connector 2 comprises a flexible hose 6, which may be bend 180 so that the catheter device and the urine bag device may be positioned side by side. In use the hose may be straightened out so that the urine bag device extends the catheter device. The catheter assembly may be provided in an outer package, which may retain the catheter device and the urine bag device in the side by side configuration.

Figure 10:
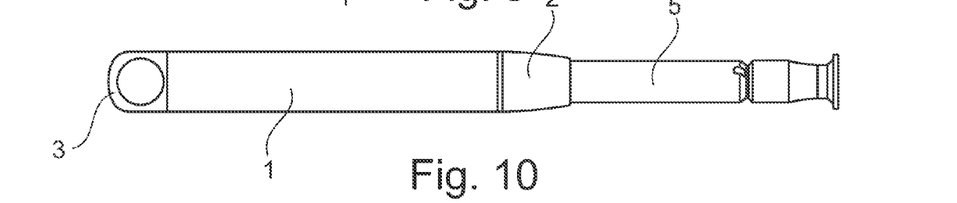
FIG. 10 illustrates a second embodiment of a catheter assembly according to the invention.

FIG. 10 shows an embodiment of the invention wherein the urine bag device is attached to the catheter device in extension thereof. The configuration shown may also be obtained with a urine bag device attachable to the catheter device.

FIG. 11 is a principle sketch of an embodiment of the invention in which the catheter device is inside the urine bag device. The urine bag is folded into itself and around the catheter device and surrounded by constraining means in the shape of a sleeve member. As the urine bag is typically much wider than the catheter device the folding of the urine bag in the compact configuration further comprises a rolling or twisting of the urine bag, to wrap the urine bag tight around the catheter device.

Figure 12:
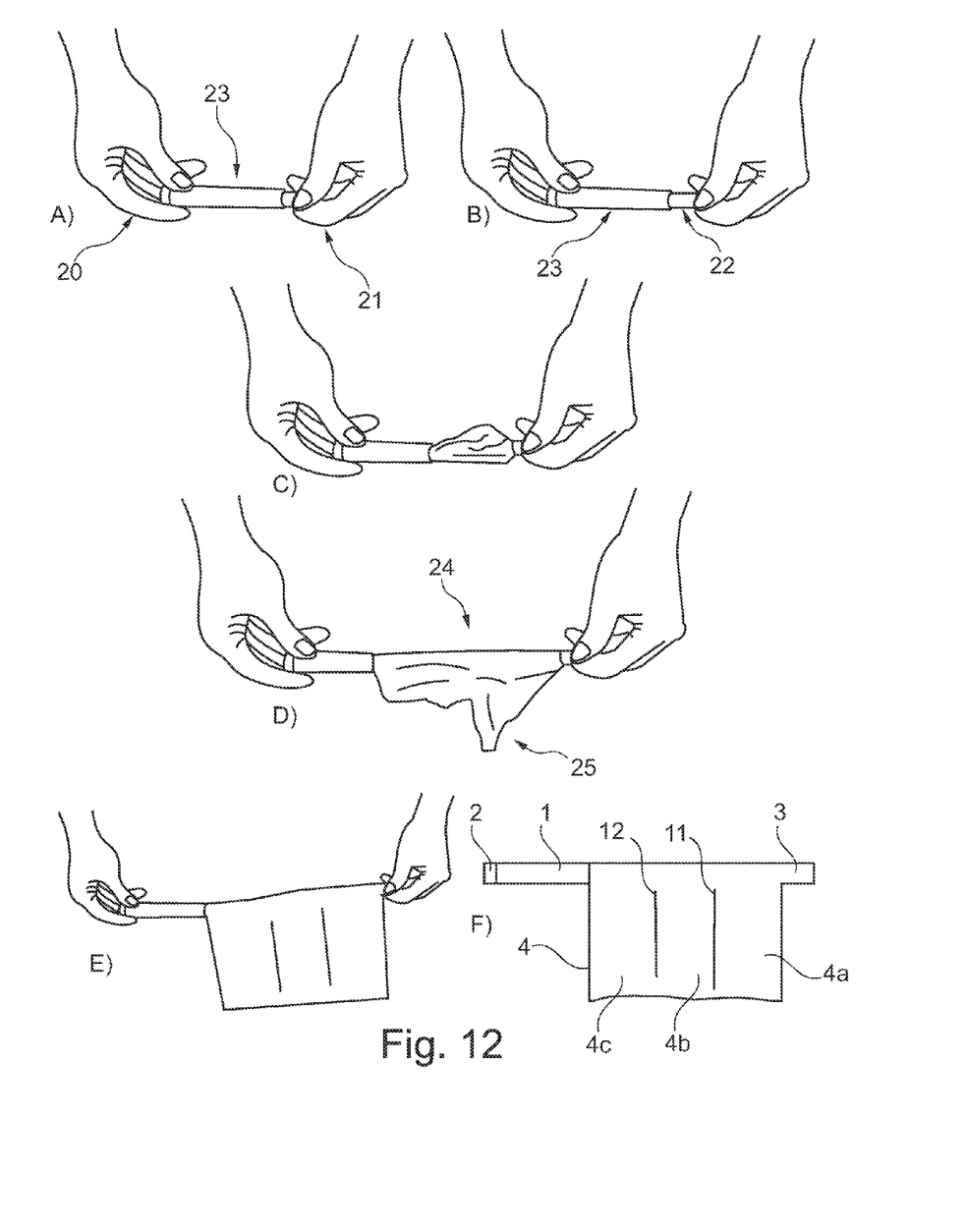
FIG. 12 illustrates the unfolding of a urine bag according to one aspect of the invention.

FIG. 12 illustrates compact bag unfolding. In this embodiment, the urine-bag is packed into a urine bag device here a sleeve member of a relatively rigid tube. The urine-bag is first Z-folded and then rolled up.

The compact bag is then unfolded as described in the following steps and with reference to FIG. 12:

A) a firm grip on two opposite pull points of the urine bag, first pull point 20 and second pull point 21.

B) during the first part of the unfolding-pull, the urine-bag 22 will be pulled out of the sleeve member 23.

C) while pulling in the same direction, i.e. out of the sleeve member, the force of unfolding the Z-fold will, while unfolding the Z-fold, unpack the rolling of the urine-bag.

D) the urine-bag is now almost unpacked. The Z-fold is fully unfolded at the top 24 of the urine-bag, while the bottom part 25 of the urine-bag is still unfolding.

E) the urine-bag is fully unpacked.

F) the unpacked urine-bag.

Figure 13:
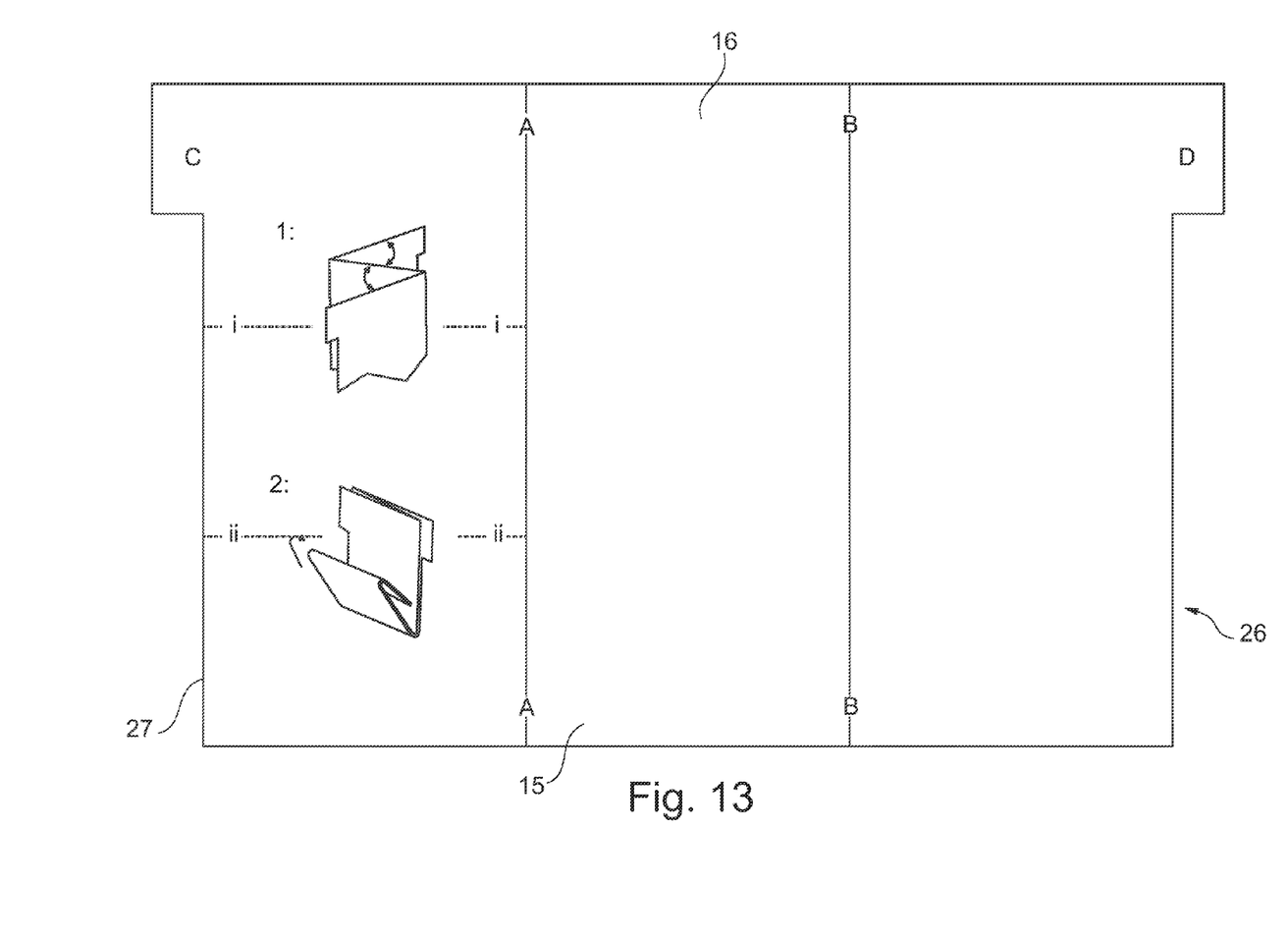
FIG. 13 illustrates a representation of one embodiment of a collecting bag suitable for cutting out.

FIG. 13 shows schematically one embodiment of the collecting bag in the form of sheet 26, which is suitable for cutting and folding in order to practically illustrate the advantage of a collecting bag folded according to the method of the invention.

First cut out the sheet 26 along the solid line 27. For orientation purposes the front of the sheet will be the side on where print is provided, while the back of the sheet is where no print is provided. There are provided tabs C and D on the side of the sheet. The area of the sheet whereon the tabs are provided is referred to as the upper end 16 and the opposite area where no tabs are provided is referred to as the lower end 15, cf. FIGS. 5 and 6.

Step 1: Fold the sheet I a first direction along dotted line B-B so that the front of the sheet is folded together. Then fold the sheet along the dotted line A-A so that the back of the sheet is folded together. This is the semi-compact state of the sheet wherein the inner folding is provided.

Step 2: Fold the lower end of the sheet up towards the upper in a second direction mainly parallel to the folding lines A-A and B-B and consecutively around folding lines ii-ii and i-i. This is the compact state of the sheet wherein the outer folding is provided.

In order to unfold the sheet pull the tabs C and D away from each other in a direction mainly identical to the first direction. As can be seen the sheet advantageously unfolds in two directions while only one pulling motion in one direction is performed.

Instead of folding in Step 1, the sheet can be crumpled and in Step 2 the sheet can alternatively be rolled or crumpled. This will still allow the sheet to unfold by pulling the tabs C and D apart.

Figure 14:
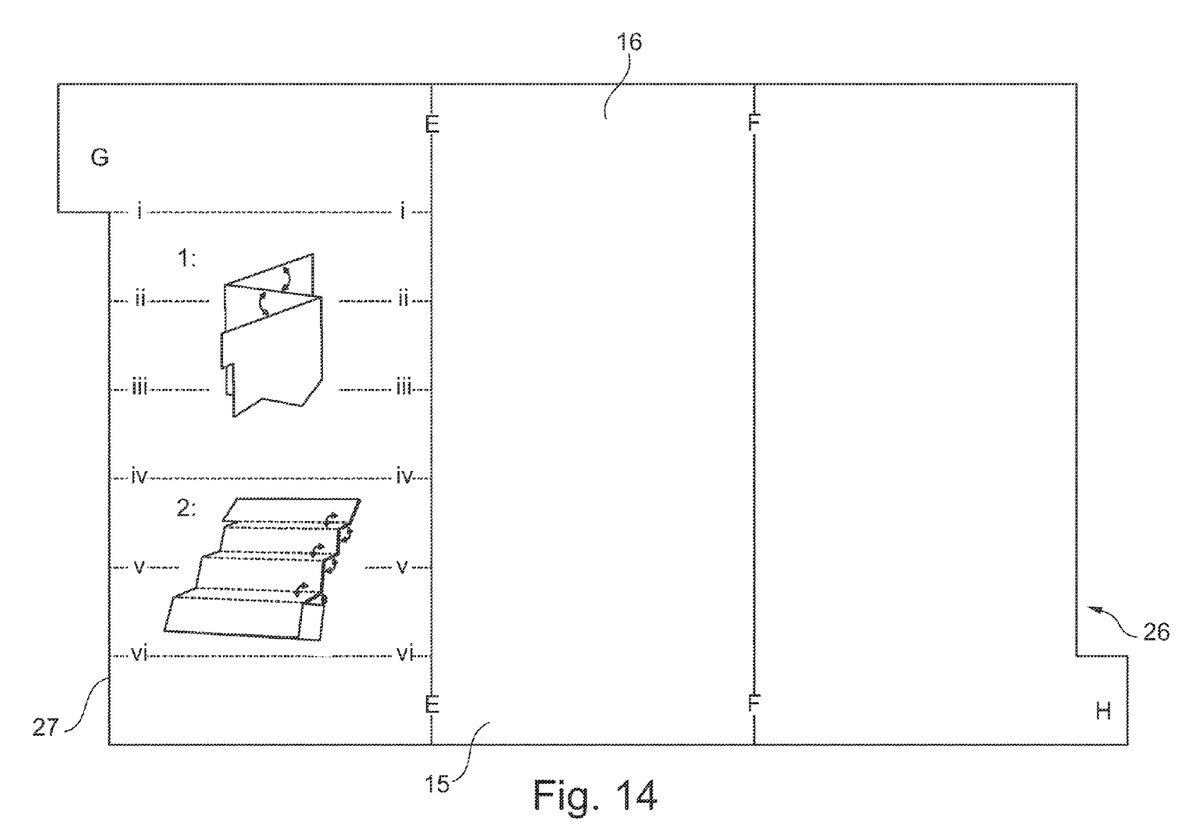
FIG. 14 illustrates another representation of another embodiment of a collecting bag suitable for cutting out.

In FIG. 14 another cut out of a sheet 28 is provided, illustrating yet another embodiment of how to fold a collecting bag according to the invention.

Cut out the sheet along the solid line 27. As in FIG. 13 the side where there is print is referred to as the front of the sheet and the side with no print is referred to as the back of the sheet. Tabs G and H are arranged at diametrically opposed corners on the sheet. The area whereon tab G is arranged will be referred to as the upper end 16 and the area whereon tab H is arranged will be referred to as the lower end 15, cf. FIGS. 5 and 6.

Step 1: Fold the sheet in a first direction along dotted line F-F so that the front of the sheet is folded together. Then fold the sheet along the dotted line E-E so that the back of the sheet is folded together. This is the semi-compact state of the sheet, wherein the inner folding is provided.

Step 2: Now fold the sheet in a second direction around the dotted line vi-vi so that the back of the sheet is folded together. Thereafter fold the sheet around the dotted line v-v so that the front of the sheet is folded together. Repeat the same steps for the dotted lines iv-iv, iii-iii, ii-ii and i-i, so that the sheet is folded respectively clockwise and counter-clockwise around the dotted lines i-i to vi-vi in consecutively order. This is the compact state of the sheet, wherein the outer folding is provided.

In order to unfold the sheet the tabs G and H are pulled apart in a direction mainly identical to the first direction. It can be seen that since one pulling point, e.g. tab G and another pulling point, e.g. tab H are arranged mainly diametrically opposite each other the sheet is further aided during unfolding.

When the collecting bag is formed according to the sheets 26,28 as described above, it is easily unfolded into its non-compact state. An opening to the collecting bag could for example be formed at the tabs C and G. A connector for connecting a urinary catheter device could for example be provided at this opening or the constraining means could be mounted hereto, for example by welding or gluing the opening and the constraining means together. The tabs D and H could function as pull point, for example provided with gripping means as described earlier.

Figure 15:
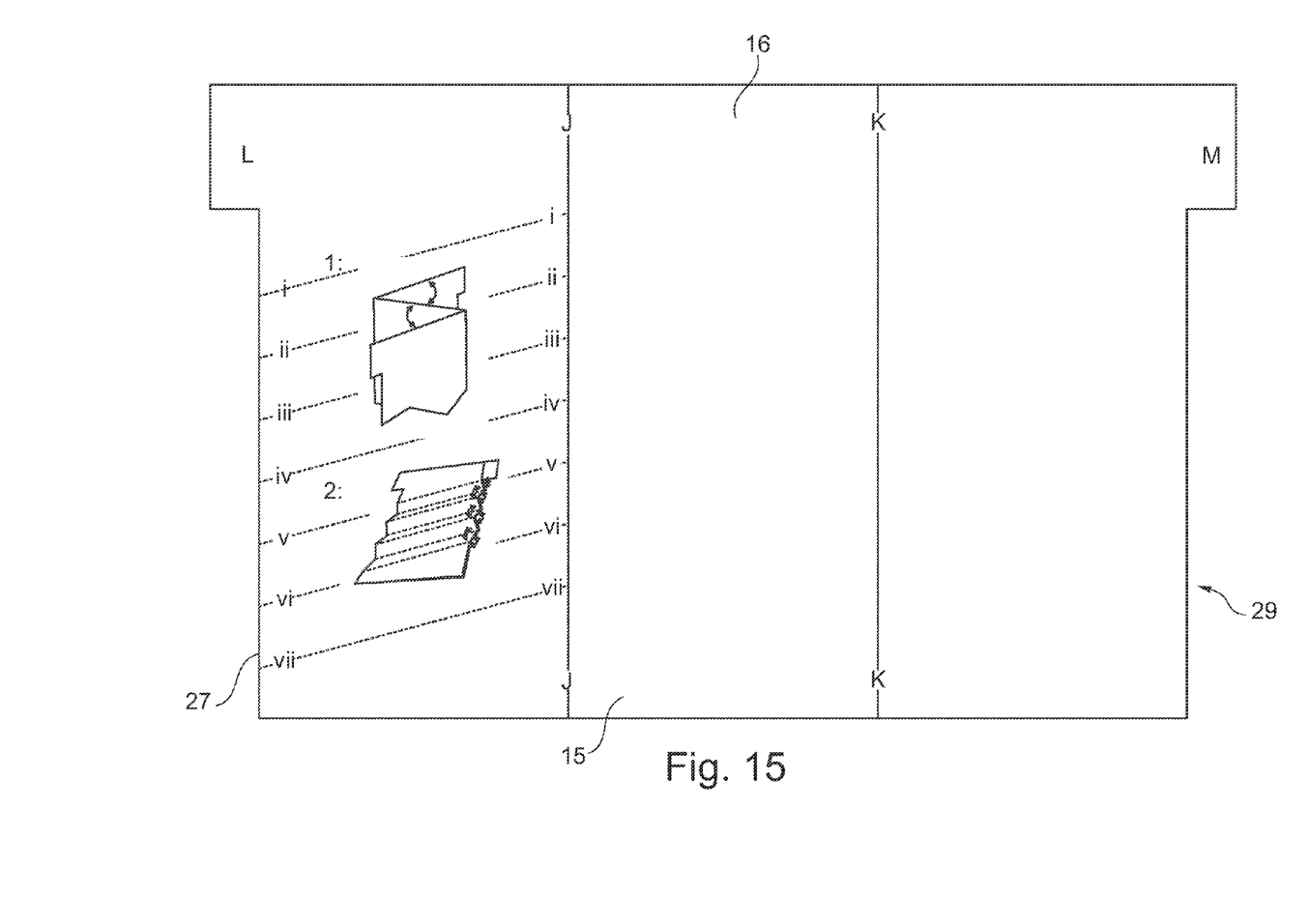
FIG. 15 illustrates yet another representation of another embodiment of a collecting bag suitable for cutting out.

In FIG. 15 yet a third cut out sheet 29 is provided representing another embodiment of a collecting bag according to the invention. The sheet 29 is cut out along the solid line 27.

Step 1: Fold the sheet in a first direction along dotted line K-K so that the front of the sheet is folded together. Then fold the sheet along the dotted line J-J so that the back of the sheet is folded together. This is the semi-compact state of the sheet, wherein the inner folding is provided.

Step 2: Now fold the sheet in a second direction around the dotted line vii-vii so that the back of the sheet is folded together. Thereafter fold the sheet around the dotted line vi-vi so that the front of the sheet is folded together. Repeat the same steps for the dotted lines v-v, vi-vi, iii-iii, ii-ii and i-i, so that the sheet is folded respectively clockwise and counter-clockwise around the dotted lines i-i to vii-vii in consecutively order. This is the compact state of the sheet, wherein the outer folding is provided.

In order to unfold the sheet pull the pulling points, i.e. tabs L and M, away from each other. The sheet will now unfold in two directions while on being pulled in one. Furthermore, as can be understood from the represented embodiment in FIG. 15 the first and second folding direction is not necessarily perpendicular to each other. The folding lines in each of the folding directions do also not have to be parallel, this is for example illustrated when the bag is crumpled in one of the folding directions where the folding lines are randomly arranged and sometimes also broken.

It should be understood that the collecting bag could be folded in many others ways within the scope of the invention than illustrated by the exemplary embodiments above.

The invention claimed is:

1. A catheter assembly comprising:
   a body fluid collecting bag including a neck, and a urinary catheter device having a portion that is dimensioned and configured for insertion into a urethra and comprising a tubular sleeve that terminates in a connector end, the neck of the body fluid collecting bag coupled to the connector end of the urinary catheter device,
   the body fluid collecting bag is configured to be compacted and stowed inside of the tubular sleeve and is dimensioned and configured to expand when removed from the tubular sleeve for collection of body fluids;
   wherein the body fluid collecting bag comprises a grip disposed opposite the neck, the grip being dimensioned and configured to provide a pull point for removal of the body fluid collecting bag from the tubular sleeve.

2. A catheter assembly according to claim 1, wherein the neck of the body fluid collecting bag extends longitudinally from the tubular sleeve.

3. A catheter assembly according to claim 1, wherein the body fluid collecting bag is adapted to collapse into and expand out from the urinary catheter device.

4. A catheter assembly according to claim 1, wherein the body fluid collecting bag is configured to be rolled and stowed inside of the tubular sleeve.

5. A catheter assembly according to claim 1, wherein the body fluid collecting bag is configured to be folded and stowed inside of the tubular sleeve.

6. A catheter assembly according to claim 5, wherein the body fluid collecting bag is configured to be consecutively folded clockwise and counter-clockwise around at least two folding lines.

7. A catheter assembly according to claim 6, wherein the body fluid collecting bag is configured to be consecutively folded clockwise and counter-clockwise around two folding lines each oriented along a different direction.

8. A catheter assembly according to claim 1, wherein the urinary catheter device is
   an intermittent catheter that is attachable to the connector end.

9. A catheter assembly according to claim 1, wherein the urinary catheter device is an indwelling catheter that is attachable to the connector end.

10. A catheter assembly according to claim 1, wherein the grip is selected from the group consisting of a ring, a flap, and a string.

* * * * *